United States Patent
Sanfilippo et al.

[11] Patent Number: 5,405,848
[45] Date of Patent: Apr. 11, 1995

[54] SUBSTITUTED THIAZOLYLAMINOTETRAHYDROPYRIDOPYRIMIDINES DERIVATIVES USEFUL AS PLATELET AGGREGATION INHIBITORS

[75] Inventors: Pauline J. Sanfilippo, Chester Springs; Mary P. Bonner, Warrington; James J. McNally, Souderton, all of Pa.

[73] Assignee: Ortho Pharmaceutical Corporation, Raritan, N.J.

[21] Appl. No.: 171,581

[22] Filed: Dec. 22, 1993

[51] Int. Cl.$^6$ .................. A61K 31/425; C07D 413/00; C07D 471/00
[52] U.S. Cl. .................. 514/258; 514/234.2; 544/117; 544/279
[58] Field of Search .................. 514/258, 234.2; 544/279, 117

[56] References Cited

U.S. PATENT DOCUMENTS

| | | | |
|---|---|---|---|
| 4,621,082 | 11/1986 | Meyer et al. | 544/279 |
| 4,735,957 | 4/1988 | Takaya et al. | 514/258 |
| 4,895,850 | 1/1990 | Gesing et al. | 514/258 |

FOREIGN PATENT DOCUMENTS 316843  5/1989  European Pat. Off. ............ 544/279

Primary Examiner—Joseph E. Evans

[57] ABSTRACT

This invention relates to substituted thiazolylaminotetrahydropyridopyrimidines derivatives of the following general formula, the substituent groups of which are as defined in the specification herein:

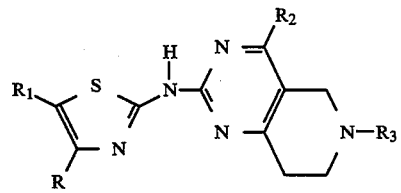

These compounds are useful as inhibitors of platelet aggregation and inhibitors of adhesion molecules and may be provided in pharmaceutical compositions and in methods of treating reperfusion thrombosis injury in patients.

15 Claims, No Drawings

SUBSTITUTED THIAZOLYLAMINOTETRAHYDROPYRIDOPYRIMIDINES DERIVATIVES USEFUL AS PLATELET AGGREGATION INHIBITORS

FIELD OF THE INVENTION

This invention relates to substituted thiazolylaminotetrahydropyridopyrimidines derivatives as described further below. These compounds are useful as inhibitors of platelet aggregation and inhibitors of adhesion molecules and may be provided in pharmaceutical compositions and in methods of treating reperfusion thrombosis injury in patients.

BACKGROUND OF THE INVENTION

Arterial thrombosis is primarily responsible for acute myocardial infarction, unstable angina and thrombotic stroke while venous thrombosis is associated with pulmonary embolism and deep vein thrombosis. A dynamic balance exists between coagulation and fibrinolysis which are regulated by the enzymes thrombin and plasmin, respectively. Superimposed on this is the process of platelet aggregation and platelet adhesion to vessel walls. Inhibition of platelet aggregation is a means of treating thrombosis for reperfusion injury. The present invention focuses on new chemical compounds which demonstrate platelet aggregation inhibition.

The present invention provides novel thiazolylaminotetrahydropyridopyrimidines compounds which are useful as inhibitors to platelet aggregation and adhesion molecules and novel intermediate compounds for producing such inhibitor compounds. The compounds of the invention are useful for treating reperfusion thrombosis injury in patients.

Various thiazole derivatives have been identified which have biological activity. For example U.S. Pat. No. 4,791,200 discloses compounds of the formula:

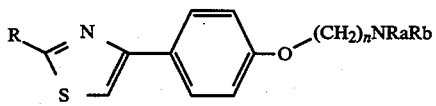

wherein R is H, alkyl, aryl or substituted phenyl and Ra and Rb are H, alkyl, aryl or substituted phenyl. These compounds are disclosed as antisecretory agents.

Chem. Pharm. Bull. 39 651–657 (1991) discloses compounds of the exempletive formula:

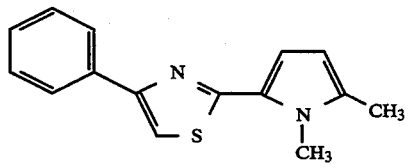

wherein thiazole derivatives are described as inhibitors of platelet aggregation via an arachidonic acid mechanism.

Sanfilippo, P. J. and Press, J. B., in U.S. Pat. No. 5,137,890 issued Aug. 11, 1992 entitled "Novel Tetrahydropyrido[4,3-d]pyrimidines as Cytoprotective Agents", disclose compounds of the formula:

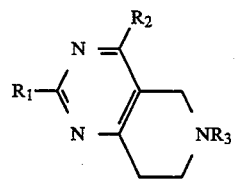

wherein $R_1$ is selected from alkyl (C1-3) or substituted amino but does not include aminothiazoles and $R_2$ is substituted phenyl and $R_3$ is independently selected from hydrogen, acyl ($C_{2-4}$), substituted benzoyl, substituted alkyl ($C_{1-4}$).

It is therefore an object of the present invention to provide novel thiazole derivatives which are useful as platelet aggregation inhibitors and their methods of use. Additional objects and advantages of the invention will be set forth, in part, in the description which follows and in part will be obvious from this description, or may be learned by practice of the invention. The objects and advantages of the invention are realized and obtained by means of the methods, and the combinations particularly pointed out in the appended claims.

SUMMARY OF THE INVENTION

To achieve the objects in accordance with the purposes of the invention, as embodied and fully described herein the present invention relates to substituted thiazolylaminotetrahydropyridopyrimidines derivatives of the following formula:

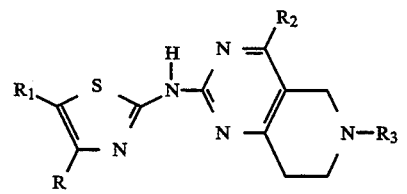

wherein R and $R_1$ are independently selected from hydrogen, alkyl ($C_1$–$C_5$), trifluoromethyl, phenyl, or substituted phenyl, wherein the phenyl substituents are selected from the group consisting of cyano, nitro, trifluoromethyl, carboxy, amino, carboxamido, tosyl, bromo, chloro, iodo, fluoro, alkyl ($C_1$–$C_5$), carboalkoxy ($C_1$–$C_4$) and alkoxy($C_1$–$C_5$);

$R_2$ is selected from the group consisting of hydrogen, alkyl ($C_1$–$C_5$), trifluoromethyl, thiophene, pyridine, phenyl or substituted phenyl wherein the phenyl substituents are selected from the group consisting of cyano, nitro, trifluoromethyl, carboxy, amino, carboxamido, tosyl, bromo, chloro, iodo, fluoro, alkyl ($C_1$–$C_5$), carboalkoxy ($C_1$–$C_4$) and alkoxy($C_1$–$C_5$);

$R_3$ is selected from hydrogen, alkyl ($C_1$–$C_4$), benzoyl or substituted benzoyl wherein the phenyl substituents are selected from the group consisting of cyano, nitro, trifluoromethyl, carboxy, amino, carboxamido, tosyl, bromo, chloro, iodo, fluoro, alkyl ($C_1$–$C_5$), carboalkoxy ($C_1$–$C_4$) and alkoxy($C_1$–$C_5$), acyl ($C_2$–$C_4$) or substituted acyl wherein the substituent may be alkyl$NR_4R_5$ wherein $R_4$ or $R_5$ may be hydrogen or alkyl ($C_1$–$C_4$) or $NR_4R_5$ forms a heterocyclic ring such as piperidine, pyrrolidine, pyrrolidinone, piperidinone, phthalimide, imidazole, or morpholine.

The present invention also includes pharmaceutically acceptable salts of the above-described compounds.

The substituted thiazolylaminotetrahydropyridopyrimidine derivatives and their pharmaceutically acceptable salts are nonpeptidal adhesion molecule antagonists which inhibit platelet aggregation. The compounds of the invention can influence cell-cell and cell-matrix interactions and can inhibit the binding of fibrinogen to the fibrinogen receptor of blood platelets. In particular, the compounds of the invention prevent the formation of blood platelet thrombi and thus may be used to control or prevent illnesses such as thrombosis, stroke, unstable angina, cardiac infarct, inflammation and arteriosclerosis. The present invention thus provides for methods of treating reperfusion thrombosis injury in a patient comprising the step of administering to a patient a platelet aggregation inhibiting effective amount of a compound as described above.

The present invention also provides for pharmaceutical compositions comprising one or more compounds as described above and a pharmaceutically inert carrier.

It is to be understood that both the foregoing general description and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following examples section. The following discloses the preferred compounds, compositions and methods of the invention.

The invention relates to substituted tetrahydropyridopyrimidinylthiazoles which have activity as adhesion molecule inhibitors which are potentially useful as anticoagulants or anti-inflammatory agents. The substituted thiazolylaminotetrahydropyridopyrimidines of the invention are prepared as outlined in the following scheme:

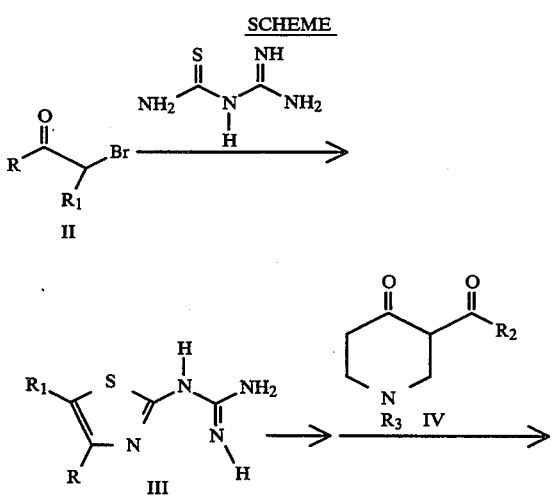

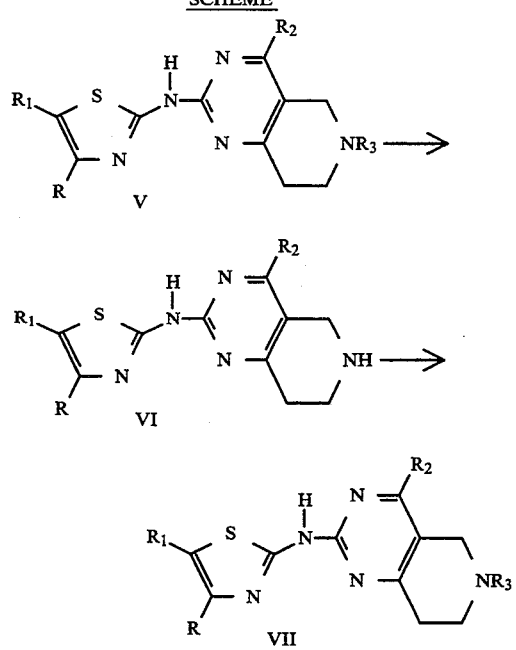

As is apparent from the foregoing reaction scheme, treatment of N-amidinothiourea with an appropriately substituted alpha-haloketone in an alcoholic solvent such as ethanol for 3–12 hours (h) gives the guanidinothiazole derivative III. Compound III is condensed with a β-diketone or β-ketoaldehyde derivative (IV $R_3=C(O)CH_3$, $C(O)Ph$), (in a suitable solvent such as acetone or ethanol at refluxing temperature for a period of 12–72 h to give the acylated thiazolylaminotetrahydropyridopyrimidine V ($R_3=C(O)CH_3$, $C(O)Ph$). The resulting acylated thiazolylaminotetrahydropyridopyrimidine V is then treated with an aqueous acid such as hydrochloric acid, sulfuric acid or p-toluenesulfonic acid, or an aqueous base such as sodium hydroxide, potassium hydroxide or sodium carbonate. The resulting secondary amine VI can be treated with an alkylating agent such as iodomethane, iodoethane, benzyl bromide, bromoalkanol or dihaloalkane, in the presence of a base such as triethylamine, potassium carbonate, sodium hydride in a suitable solvent such as methylene chloride, tetrahydrofuran, dimethylformamide, dimethyl sulfoxide at 10° C. to 100° C. to give the thiazolylaminotetrahydropyridopyrimidine derivatives VII. Alternatively, the secondary amine VI can be treated with an acylating agent such as chlorobutrylchloride chloropropionylchloride, in the presence of a base such as triethylamine and the resulting chloride can be displaced with an appropriately substituted nucleophile such as pyrrolidinone, imidazole, methyl piperazine or propylamine to give the N-substituted thiazolylamino-tetrahydropyridopyrimidine derivatives VII.

The following examples describe the invention in greater detail and are intended to be a way of illustrating but not limiting the invention.

EXAMPLES

The invention will now be illustrated by examples. The examples are not intended to be limiting of the scope of the present invention. In conjunction with the detailed and general description above, the examples provide further understanding of the present invention and outline a process for producing the compounds of the invention.

The following examples represent preferred embodiments of the compounds, compositions, processes and methods of the invention for satisfying the stated objects of the invention.

Melting point determinations were carried out on a Thomas Hoover capillary melting point apparatus and are uncorrected. All compounds had spectra (elemental analysis, IR, $^1$H NMR, MS) consistent with their assigned structures. Nuclear magnetic resonance (NMR) spectra for hydrogen atoms were measured in the indicated solvent with tetramethylsilane (TMS) as the internal standard on a GE QE-300 spectrometer. The values are expressed in parts per million downfield from TMS. Elemental analyses were determined on a Perkin Elmer 2400 spectrometer and are expressed in percentage by weight of each element per total molecular weight and such found values are reported in the tables and are consistent with the assigned structures. The mass spectra (MS) were determined on a Finnigan Mat 8230 or a Finnigan Mat INCOS 50, single stage, quadrupole using desorption chemical ionization techniques. All column chromatography was run using Silica Gel 60, 230–400 mesh and any appropriate commercially available solvent. Unless otherwise noted, the materials used in the examples and substitutes therefor are obtained from readily available commercial suppliers or synthesized by standard methods known to anyone skilled in the art of chemical synthesis. The substituent groups, which vary between examples are assumed to be hydrogen unless otherwise noted.

Example Intermediate I (Int 1)

2-Amidino-4-(3-trifluoromethylphenyl)thiazole Hydrobromide

N-Amidinothiourea (0.663 g, 5.62 mM) was added to a solution of 3(trifluoromethyl)phenacylbromide (1.5 g, 5.62 mM) in EtOH (10 mL) and the reaction mixture was heated at reflux for 3 hours (h). The mixture was concentrated in vacuo to one half volume and the resulting solid precipitate was isolated. This solid was washed with EtOH and dried in vacuo to give the title compound as a solid: melting point (mp) 219°–221° C.; $^1$H NMR (DMSO d$_6$): δ 8.28 (m, 5H), 8.07 (s, 1H), 7.71 (m, 2H); MS: 287 (MH+).

The following general procedure was used in the synthesis of the compounds listed in Table 1. N-Amidinothiourea (1 Molar Equivalent) was added to a solution of an appropriately substituted bromoketone derivative II (1 Molar Equivalent) in a suitable solvent and the reaction mixture was heated at reflux for 3–12 h. The mixture was concentrated in vacuo to one half volume and the resulting solid precipitate was isolated. This solid was washed with an appropriate solvent and dried in vacuo to give the desired compound III as the hydrobromide salt.

TABLE 1

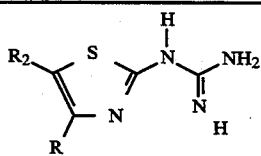

TABLE 1-continued

| Intermediate | R | R$_2$ | mp, °C. |
|---|---|---|---|
| Int 2 | Ph | H | 208–209 |
| Int 3 | 3-ClPh | H | 223–224 |
| Int 4 | 4-CH$_3$Ph | H | 283–286 |
| Int 5 | 4-ClPh | H | 279–281 |

COMPOUND 1 (CMPD 1)

6-Acetyl-2-[4-phenylthiazol-2-yl]amino-5,6,7,8-tetrahydro-4-phenylpyrimidino[4,5-d]pyridine To 2-guanidino-4-phenylthiazole hydrobromide (13.14 g, 0.044 mol) was added acetone (240 mL), with stirring. Triethylamine (4.45 g, 6.3 mL, 0.044 mol) was added. The resulting solution was heterogeneous. N-Acetyl-3-benzoyl-4-piperidone (7.18 g, 0.029 mol) was dissolved in acetone (30 mL), with gentle warming, then added to the guanidino phenylthiazole solution. The reaction mixture was heated at reflux for three days. The solid which had precipitated was filtered in a sintered glass funnel, and washed with water to remove triethylamine hydrobromide. The remaining solid, composed of the desired product along with a small amount of the excess starting guanidino phenylthiazole, was recrystallized from methanol to give 3.29 g (7.7 mmol) of the title compound as a tan solid; mp 130°–132° C. A second crop precipitated from the mother liquor and was recrystallized from methanol to give an additional 2.7 g (6.3 mmol). The combined yield was 48%.

The following general procedure was used to synthesize the compounds listed in the Table 2 (R$_2$≠H): To the appropriately substituted 2-guanidino-4-phenylthiazole hydrobromide (30 mmol) was added acetone (100 mL). Triethylamine (2.1 molar equivalents) was added. The β-diketone or β-ketoaldehyde (IV, 19 mmol) was dissolved in acetone (50 mL) and added to the guanidino phenylthiazole solution. The reaction mixture was heated at reflux for 3 days. The solid which had precipitated was filtered in a sintered glass funnel and washed with water to remove the triethylamine hydrobromide. The remaining solid, containing the excess guanidino phenylthiazole, was recrystallized from methanol to give the desired 6-acylated-2-[4-(substituted phenyl)thiazol-2-yl]amino-5,6,7,8-tetrahydro-4phenylpyrimidino[4,5-d ]pyridine.

The following general procedure was used to synthesize compound IV (R$_2$≠H): Into a dried, 3-neck flask fitted with a mechanical stirring device, an addition funnel and a low temperature thermometer was cannulated lithium hexamethyldisilazane (1.0 M in THF, 1.1 molar equiv). The solution was cooled via a dry ice-/acetone bath. A solution of N-benzoyl-4piperidone (1.0 equiv) in THF (50 mL) was added dropwise, with stirring, over thirty minutes. The solution was stirred at −72° to −68° C. for thirty minutes. Ethyl formate (2 equiv) was added all at once and the solution stirred at −70° C. for ten minutes, then at room temperature for twenty eight hours. The solution was treated with 1N HCl (200 mL) and extracted (methylene chloride and brine). The extracts were dried (MgSO$_4$) and concentrated to yield 3-formyl-4-piperidone as an orange oil (73%).

TABLE 2

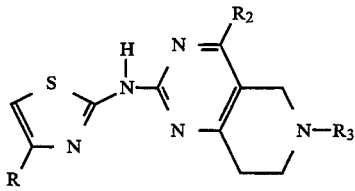

| Cmpd | R | R$_2$ | R$_3$ | mp, °C. |
|---|---|---|---|---|
| 2 | 3-CF$_3$Ph | Ph | C(O)Me | 197–198 |
| 3 | Ph | thienyl | C(O)Me | 229–230 |
| 4 | 3-ClPh | Ph | C(O)Me | 146–148 |
| 5 | 4-MePh | Ph | C(O)Me | 230–232 |
| 6 | 4-MeOPh | Ph | C(O)Me | 243–245 |
| 7 | 3-CF$_3$Ph | H | C(O)Ph | 249–251 |
| 8 | 4-FPh | Ph | C(O)Me | 203–206 |
| 9 | 4-FPh | Ph | C(O)Ph | 265–266 |
| 10 | 4-ClPh | Ph | C(O)Ph | 273–275 |
| 11 | 4-CF$_3$Ph | Ph | C(O)Me | 215–216 |
| 12 | Ph | CF$_3$ | C(O)Ph | 229–231 |

CMPD 13

2-[4-Phenylthiazol-2-yl]amino-5,6,7,8-tetrahydro-4-phenylpyrimidino[4,5-d]pyridine 6-Acetyl-2-[4-phenylthiazol-2-yl]amino-5,6,7,8-tetrahydro-4-phenylpyrimidino[4,5-d]pyridine (2.68 g, 6.29 mmol) was treated with a 15% solution of HCl in water (135 mL) and ethanol (200 mL). The solution was heated to reflux for 22 h. The solution was cooled, then concentrated to give the HCl salt of the title compound as a yellow solid. The free base was obtained by treatment with saturated sodium bicarbonate, at 0° C., until the solution became colorless. The white solid was filtered then dried. Recrystallization from methanol gave 1.19 g (49%) of the title compound as an off-white solid; mp 245°–246° C. Similarly, compounds of Table 3 were prepared in accordance with this general procedure.

TABLE 3

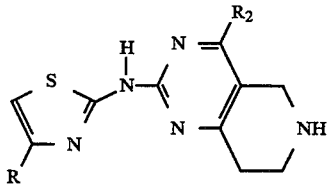

| Cmpd | R | R$_2$ | mp, °C. |
|---|---|---|---|
| 14 | 3-CF$_3$Ph | Ph | 132–134 |
| 15 | 4-MePh | Ph | 240–243 |
| 16 | 3-ClPh | Ph | 129–131 |
| 17 | 3-CF$_3$Ph | H | 267–270 |
| 18 | 4-MeOPh | Ph | 271–272 |
| 19 | 4-MeOPh | H | 255–258 |
| 20 | 4-FPh | Ph | 215–217 |
| 21 | 4-ClPh | Ph | 281–283 |
| 22 | 4-FPh | H | 298–300 |
| 23 | 4-MePh | H | 304–307 |
| 24 | Ph | H | 311–313 |
| 25 | Ph | CF$_3$ | 274–277 |

CMPD 26

6-[3-N-Methylpiperazino)-1-propanon-1-yl]-2-[4-(4-methylphenyl)thiazol-2-yl]amino-5,6,7,8-tetrahydro-4-phenylpyrimidino[4,5-d]pyridine 2-[4-[4-Methylphenyl]thiazol-2-yl]amino-5,6,7,8-tetrahydro-4-phenylpyrimidino[4,5-d]pyridine (0.287 g, 0.718 mmol) was treated with methylene chloride (10 mL) and triethylamine (0,100 mL, 0.718 mmol). A solution of 3-chloropropionyl chloride (0.069 mL, 0.718 mmol) in methylene chloride (10 mL) was added to the reaction mixture, resulting in a clear, colorless solution. The reaction mixture was stirred overnight. 1-Methylpiperazine (1.8 mL, 2.88 mmol) was added, and the solution was stirred overnight. The solution was concentrated to give an oil, which was extracted with ethyl acetate and saturated sodium bicarbonate (3×), then brine (2×) The ethyl acetate solution was dried and concentrated to give 0.327 g (82%) of the title compound as a white solid; mp 134°–136° C. Similarly, compounds of Table 4 were prepared in accordance with this general procedure.

TABLE 4

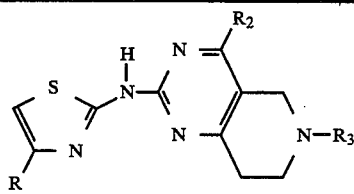

| Cmpd | R | R$_2$ | R$_3$ | mp, °C. |
|---|---|---|---|---|
| 27 | 4-MePh | Ph | C(O)(CH$_2$)$_2$NHPr | 219–220 |
| 28 | 3-ClPh | Ph | C(O)(CH$_2$)$_2$NHPr | 216–218 |

BIOLOGICAL ASSAYS

Platelet Aggregation Inhibition Activity

The percentage of platelet aggregation is calculated as an increase in light transmission of drug treated platelet concentrate vs control treated platelet concentrate. Blood is obtained from drug free, normal donors and placed into tubes containing 0.13 M sodium citrate (two sources are routinely used: platelet concentrate obtained from Biological Specialty Corp., Lansdale, Pa. or whole blood obtained from donors). Platelet rich plasma (PRP) is collected by centrifugation of the concentrate or whole blood at 130 ×g for 15 min at 25° C. The PRP (5 mL) is gel filtered through Sepharose 2B (bed volume 50 mL), and the platelet count is adjusted to 2×10$^7$ platelets per sample. The following constituents are added to a siliconized cuvette: 250 μL of the concentrated platelet flitrate, 100 μL of Tyrode's buffer (0.14 M NaCl, 0.0027 M KCl, 0.012 M NaHCO$_3$, 0.76 mM Na2HPO$_4$, 0.0055 M glucose and 2 mg/mL BSA pH 7.4), 50 μL of 2 mM calcium and test drug (50 mL). Aggregation is monitored in a dual channel Chrono-log Aggregometer for three minutes following the addition of agonist (thrombin 50 μL of 1 unit/mL, or ADP 50 μL of 100 μM). The final assay volume is 500 μL. The reaction takes place at 37° C. The peak aggregation response is calculated as the increase in light transmission units over a three minute period. The difference of the increase in light transmission between control and drug treated platelets is then expressed as a percent of the nondrug treated controls. The percentage of inhibition of platelet aggregation of certain selected compounds at 20 μM is displayed in Table 5.

Fibrinogen Binding

The compounds of the invention as identified above are evaluated for platelet aggregation inhibition activity as indicated by the percentage of non-aggregated platelets which are available for binding in accordance with the following procedure.

$^{125}$I-Fibrinogen binding to activated platelets is a modification of the procedure described by Bennett et al., 1988. Briefly, 40 mL of PRP are centrifuged at 120 ×g to remove contaminating red cells. Aspirin (50 μM) is added and the PRP is incubated at 37° C. for 20 minutes. The pH of the PRP is adjusted to 6.5 with 3.8% sodium citrate and 0.9 μM of PGE1 is added. Platelets are concentrated by a 300 ×g centrifugation (10 min) and the pellet is resuspended in 4 mL. of Tyrode's buffer. The platelet suspension (4 mL) is gel-filtered through a Sepharose-2B column (50 mL bed volume). The platelet count is adjusted to 1×108 platelets per 200 mL. The binding reaction is performed in polystyrene tubes (final volume 500 mL). Reagents are added in the following order: 80 mL of Tyrode's buffer, 50 mL of CaCl$_2$ (final concentration (f.c.) 0.2 μM) and 50 mL of thrombin (f.c. 0.1 unit/mL). The platelet suspension is then added and the mixture is allowed to incubate at room temperature for 2 minutes. Hirudin (50 mL, f.c. 0.5 unit/mL) is immediately added to prevent the catalytic activity of thrombin. Various concentrations of the compound to be tested (50 mL) with the competing radioligand $^{125}$I-fibrinogen (f.c. of 0.15 μM) are added. The mixture is incubated for 10 minutes at room temperature. To terminate the binding reaction the platelets are sedimented (10,000 ×g for 3 minutes) through silicone oil (3:1 hi-phenol 550/methyl silicone 200, W. F. Nye, Inc., New Bedford, Mass.), in an Eppendorf centrifuge.

The tips of the centrifuge tubes containing the pelleted platelets are cut off and counted for $^{125}$I-fibrinogen associated with the stimulated platelets. The amount of platelet radioactivity measured in the presence of nonlabeled fibrinogen (4 mg/mL) is considered the nonspecific binding.

Data are expressed as a percent at concentrations of 30 μM of specifically bound $^{125}$I-fibrinogen to the platelets in Table 5 below. Positive percentages of fibrinogen binding indicates higher activity for inhibiting platelet aggregation since only non-aggregated or free platelets are available for fibrinogen binding. Alternatively, a concentration is provided in lieu of a percentage to indicate the IC$_{50}$ of concentration of compound which provides 50% fibrinogen binding.

TABLE 5

| Cmpd | % Inhibition Platelet Aggregation @ 20 μM | % Inhibition Fibrinogen Binding @ 30 μM |
|---|---|---|
| 9 | 27% | |
| 15 | 85% | 28% |
| 18 | 25% | |
| 13 | 100% IC50 = 7.93 | 69% IC50 = 7.7 |
| 20 | 87% IC50 = 5.8 | 95% IC50 = 20.9 |
| 21 | 84% IC50 = 6.1 | 87% IC50 = 20.9 |
| 23 | 25% | |
| 24 | 11% | |
| 26 | 81% | 39% |
| 28 | 56% | |

The above test results demonstrate the utility of the compounds of the invention for inhibiting platelet aggregation. The scope of the present invention is not limited by the description, examples and suggested uses described herein and modifications can be made without departing from the spirit of the invention. For example, additional medicaments or active components may be used in combination with the compounds of the invention or two or more compounds of the invention may be used in combination in a pharmaceutical composition. Further, the novel compounds of the invention may have other uses in addition to those described herein.

Pharmaceutical compositions containing compounds of the invention may comprise the compound of the present invention and a pharmaceutically acceptable carrier in either solid or liquid form. Solid form preparations include powders, tablets, dispersible granules, capsules, etc. The carrier may also be one or more substances which act as diluents, flavoring agents, solubilizers, lubricants, suspending agents, binders, or tablet disintegrating agents as well as encapsulating materials. Suitable carriers are magnesium carbonate, magnesium stearate, talc, lactose, sugar, peptin, dextrin, starch, methylcellulose, sodium carboxymethylcellulose, and the like. Liquid form preparations include solutions which are suitable for oral or parenteral administration, or suspensions and emulsions suitable for oral administration.

Sterile water solutions of the active component or sterile solutions of the active components in solvents comprising water, ethanol, or propylene glycol are examples of liquid preparations suitable for parenteral administration. Sterile solutions may be prepared by dissolving the active component in the desired solvent system, then passing the resulting solution through a membrane filter to sterilize it, or alternatively, by dissolving the sterile compound in a previously sterilized solvent under sterile conditions. Aqueous solutions for oral administration can be prepared by dissolving the active compound in water and adding suitable flavorants, coloring agents, stabilizers and thickening agents as required. Aqueous suspensions for oral use can be made by dispersing the finely divided active component in water together with a viscous material such as a natural or synthetic gum, methyl cellulose, sodium carboxy methyl cellulose, and other suspending agents known to the pharmaceutical formulation art.

It is especially advantageous to formulate the aforementioned pharmaceutical compositions in unit dosage form for ease of administration and uniformity of dosage. The term "unit dosage form" as used herein refers to physically discrete units suitable as unit dosages, each unit containing a predetermined quantity of active ingredient calculated to produce the desired therapeutic effect in association with the required pharmaceutical carrier.

Various conventional techniques for preparing pharmaceutical compositions including solutions, suspensions, tablets or caplets can be employed, as would be known to those skilled in the art and as is disclosed for example by *Remington's Pharmaceutical Sciences.*, Mack Publishing Co., Part 8 Chapters 76–93, "Pharmaceutical Preparations and Their Manufacture", pp. 1409–1677 (1985).

In therapeutic use as inhibitors of platelet aggregation and/or fibrinogen binding, the compounds utilized in the methods of this invention may be administered to a patient either orally or parenterally at dosage levels from about 1–100 mg/kg and preferably about 3–10 mg/kg of body weight per day. The dosages, however, may be varied depending upon the results of specific clinical testing, the requirements of the patient, the weight and age of the patient, the severity of the condition being treated, and the compound being employed.

Determination of optimum dosages for a particular situation is within the skill of the art.

Applications of the compounds, compositions, and methods of the present invention for medical or pharmaceutical uses can be accomplished by any clinical, medical, and pharmaceutical methods and techniques as are presently or prospectively known to those skilled in the art. Thus it is intended that the present invention cover any modifications and variations of this invention provided that they come within the scope of the appended claims and their equivalents.

What is claimed is:

1. A compound of the formula:

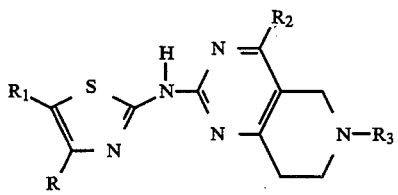

wherein R and $R_1$ are independently selected from hydrogen, alkyl ($C_1$-$C_5$), trifluoromethyl, phenyl, or substituted phenyl, wherein the phenyl substituents are selected from the group consisting of cyano, nitro, trifluoromethyl, carboxy, amino, carboxamido, tosyl, bromo, chloro, iodo, fluoro, alkyl ($C_1$-$C_5$), carboalkoxy ($C_1$-$C_4$) and alkoxy($C_1$-$C_5$);

$R_2$ is selected from the group consisting of hydrogen, alkyl ($C_1$-$C_5$), trifluoromethyl, thiophene, pyridine, phenyl or substituted phenyl wherein the phenyl substituents are selected from the group consisting of cyano, nitro, trifluoromethyl, carboxy, amino, carboxamido, tosyl, bromo, chloro, iodo, fluoro, alkyl ($C_1$-$C_5$), carboalkoxy ($C_1$-$C_4$) and alkoxy($C_1$-$C_5$);

$R_3$ is selected from hydrogen, alkyl ($C_1$-$C_4$), benzoyl or substituted benzoyl wherein the phenyl substituents are selected from the group consisting of cyano, nitro, trifluoromethyl, carboxy, amino, carboxamido, tosyl, bromo, chloro, iodo, fluoro, alkyl ($C_1$-$C_5$), carboalkoxy ($C_1$-$C_4$) and alkoxy($C_1$-$C_5$), acyl ($C_2$-$C_4$) or substituted acyl wherein the substituent is alkyl $NR_4R_5$ wherein $R_4$ or $R_5$ is hydrogen or alkyl ($C_1$-$C_4$) or $NR_4R_5$ forms a heterocyclic ring selected from the group consisting of piperidine, pyrrolidine, pyrrolidinone, piperidinone, phthalimide, imidazole, piperazine and morpholine; and pharmaceutically acceptable salts thereof.

2. A compound according to claim 1 wherein:

R and $R_1$ are independently selected from hydrogen, phenyl, or substituted phenyl, wherein the phenyl substituents are selected from the group consisting of trifluoromethyl, bromo, chloro, fluoro, methyl and methoxy;

$R_2$ is selected from the group consisting of hydrogen, trifluoromethyl, thiophene or phenyl;

$R_3$ is selected from hydrogen, benzoyl, acyl or substituted acyl wherein the substituent is alkyl$NR_4R_5$ wherein $R_4$ or $R_5$ is hydrogen or alkyl ($C_1$-$C_4$) or $NR_4R_5$ is piperazine; and pharmaceutically acceptable salts thereof.

3. A compound according to claim 2 of the formula:
6-Benzoyl-2-[4-(4-fluorophenyl)thiazol-2-yl]amino-5,6,7,8-tetrahydropyrimidino[4,5-d]pyridine.

4. A compound according to claim 2 of the formula:
2-[4-(4-Methylphenyl)thiazol-2-yl]amino-5,6,7,8-tetrahydropyrimidino-[4,5d]pyridine;
2-[4-(4-Chlorophenyl)thiazol-2-yl]amino-5,6,7,8-tetrahydro-4-phenylpyrimidino[4,5-d]pyridine;
2-[4-(4-Fluorophenyl)-thiazol-2-yl]-amino-5,6,7,8-tetrahydro-4-phenylpyrimidino[4,5-d]pyridine;
2-[4-(4-Methoxy-phenyl)thiazol-2-yl]amino-5,6,7,8-tetrahydro-4-phenyl-pyrimidino-[4,5-d]pyridine;
2-[4-(4-Methylphenyl)thiazol-2-yl]amino-5,6,7,8-tetrahydro-4-phenylpyrimidino[4,5-d]pyridine; and
2-[4-Phenyl-thiazol-2-yl]amino-5,6,7,8-tetrahydro-4-phenylpyrimidino[4,5-d]pyridine.

5. A compound according to claim 2 of the formula:
6-[3-N-Methylpiperazino)-1-propanon-1-yl]-2-[4-(4-methylphenyl)thiazol-2yl]amino-5,6,7,8-tetrahydro-4-phenylpyrimidino[4,5-d]pyridine;
6-[3-N-Propylamino)-1-propanon-1-yl]-2-[4-(3-chlorophenyl)thiazol-2-yl]-amino-5,6,7,8-tetrahydro-4-phenylpyrimidino[4,5-d]pyridine; and
6-[3-N-Propylamino)-1-propanon-1-yl]-2-[4-(4-methylphenyl)thiazol-2-yl]5,6,7,8-tetrahydro-4-phenylpyrimidino[4,5-d]pyridine.

6. A method of treating reperfusion thrombosis injury in a patient comprising the step of administering to a patient an amount of a compound of claim 1 effective to inhibit platelet aggregation.

7. A method of treating reperfusion thrombosis injury in a patient comprising the step of administering to a patient an amount of a compound of claim 2 effective to inhibit platelet aggregation.

8. A method of treating reperfusion thrombosis injury in a patient comprising the step of administering to a patient an amount of a compound of claim 3 effective to inhibit platelet aggregation.

9. A method of treating reperfusion thrombosis injury in a patient comprising the step of administering to a patient an amount of a compound of claim 4 effective to inhibit platelet aggregation.

10. A method of treating reperfusion thrombosis injury in a patient comprising the step of administering to a patient an amount of a compound of claim 5 effective to inhibit platelet aggregation.

11. A pharmaceutical composition comprising a compound of claim 1 and a pharmaceutically inert carrier.

12. A pharmaceutical composition comprising a compound of claim 2 and a pharmaceutically inert carrier.

13. A pharmaceutical composition comprising one or more compounds of claim 2 and a pharmaceutically inert carrier.

14. A pharmaceutical composition comprising a compound of claim 4 and a pharmaceutically inert carrier.

15. A pharmaceutical composition comprising a compound of claim 5 and a pharmaceutically inert carrier,

* * * * *